United States Patent [19]

Markert et al.

[11] 4,452,862
[45] Jun. 5, 1984

[54] PHARMACEUTICAL COATING MATERIALS SOLUBLE OR SWELLABLE IN GASTRIC JUICE AND PHARMACEUTICAL DOSAGE FORMS COATED THEREWITH

[75] Inventors: Gerhard Markert, Ober-Ramstadt; Dieter Dreher, Bickenbach; Klaus Lehmann, Rossdorf; Werner Siol, Pfungstadt; Hubert Rauch, Weiterstadt, all of Fed. Rep. of Germany

[73] Assignee: Rohm GmbH Chemische Fabrik, Darmstadt, Fed. Rep. of Germany

[21] Appl. No.: 345,478

[22] Filed: Feb. 3, 1982

[30] Foreign Application Priority Data

Feb. 20, 1981 [DE] Fed. Rep. of Germany ....... 3106449

[51] Int. Cl.$^3$ ............................................... B32B 5/16
[52] U.S. Cl. ..................................... 428/407; 524/365; 524/385; 524/391; 524/548; 524/555; 524/312; 424/33
[58] Field of Search ............... 524/365, 385, 391, 548, 524/555; 526/312; 424/33; 428/407

[56] References Cited

U.S. PATENT DOCUMENTS

| | | | |
|---|---|---|---|
| 3,959,540 | 5/1976 | Leiberich et al. | 428/35 |
| 4,036,768 | 7/1977 | Crawford et al. | 252/51.5 A |
| 4,180,519 | 12/1979 | Neel et al. | 260/459 A |
| 4,234,565 | 11/1980 | Flodin et al. | 424/33 |
| 4,297,185 | 10/1981 | Cherreux et al. | 204/159.15 |
| 4,325,862 | 4/1982 | Schuster | 524/87 |

Primary Examiner—Joseph L. Schofer
Assistant Examiner—Bernard Lipman
Attorney, Agent, or Firm—Oblon, Fisher, Spivak, McClelland & Maier

[57] ABSTRACT

Coating materials for pharmaceutical dosage forms contain, besides the conventional liquid or solid additives for pharmaceutical coatings, a binder comprising a synthetic polymer, prepared by emulsion polymerization, having 5 to 100% by weight of units derived from monomers of the formula

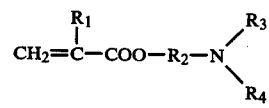

wherein $R_1$ is a hydrogen atom or a lower alkyl group, $R_2$ is an alkylene or aralkylene group having at least 3 carbon atoms in the chain between the amino nitrogen and the ester oxygen atom of which at least one is tertiary or quaternary, and $R_3$ and $R_4$ are lower alkyl radicals or together with the amino-nitrogen atom form a heteroaliphatic ring, and, optionally, additional comonomer units.

7 Claims, No Drawings

PHARMACEUTICAL COATING MATERIALS SOLUBLE OR SWELLABLE IN GASTRIC JUICE AND PHARMACEUTICAL DOSAGE FORMS COATED THEREWITH

BACKGROUND OF THE INVENTION

1. Field of the Invention

The invention relates to coating materials for pharmaceutical dosage forms which are soluble or swellable in gastric juices, and more particulaly to such coating materials which contain as binders polymers of aminoalkyl esters of acrylate or methacrylate acids and optional additional co-monomers prepared by emulsion polymerization.

2. Description of the Prior Art

Binders of this general type are known from German Pat. No. 2,135,073. The aminoalkyl esters therein disclosed for preparing such polymers by emulsion polymerization uniformly contain 2 carbon atoms between the amino-nitrogen atom and the ester-oxygen atom. The only disclosed co-monomer departing from this structure is the 4-(dimethylamino)butyl ester. In the preparation of the polymers from these monomers by emulsion polymerization, difficulties can arise because these monomers are readily soluble in water, especially the most commonly used one, dimethylaminoethyl methacrylate. A portion of the monomers can homopolymerize in the aqueous phase to form water-soluble homopolymers, and if these become bound to the latex particles or enclosed in them in the course of polymerization, they can greatly effect the solubility of the pharmaceutical coatings prepared from the latex. Furthermore, these monomers having short or unbranched alkylene groups in the aminoalkyl radical have a tendency to hydrolyze, which can occur any time before the monomer is incorporated into the polymer. As a result of this hydrolysis, acrylic or methacrylic acid is formed which is also incorporated into the polymer and alters the solubility properties. Because of these drawbacks, polymers containing more than 55% by weight of aminoalkyl esters of this type could not be prepared by emulsion polymerization, and those which contain more than 30% by weight of aminoalkyl esters can be prepared only with difficulty.

Therefore, a need has continued to exist for polymers suitable for use as binders in pharmaceutical coating materials, which can be prepared by emulsion polymerization, and which are not subject to the drawbacks of the known emulsion polymers which are used for this purpose.

SUMMARY OF THE INVENTION

Accordingly, it is an object of this invention to prepare polymers suitable for use as binders in pharmaceutical coatings.

A further object is to provide polymers from alkylamino acrylates and methacrylates which are not subject to hydrolysis during emulsion polymerization.

A further object is to provide polymers from monomers which do not homopolymerize to form water soluble polymers during emulsion polymerization.

A further object is to provide polymers, suitable for use as binders in pharmaceutical dosage forms, which are soluble in gastric juice.

Further objects of this invention will be apparent from the description of the invention which follows.

It has now been found that the objects of this invention can be achieved by polymers containing amino esters of the following formula

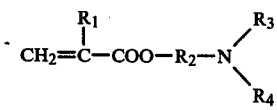

wherein $R_1$ is a hydrogen atom or a lower alkyl group, $R_2$ is an alkylene or aralkylene group having at least three carbon atoms in a straight chain between the amino-nitrogen atom and the ester-oxygen atom, at least one of which carbon atoms is tertiary or quaternary, and $R_3$ and $R_4$ are lower alkyl groups or together with the amino-nitrogen atom form a heteroaliphatic ring. Lower alkyl, in the context of this application, means alkyl groups having 1–4 carbon atoms.

Amino esters of this formula are less soluble in water than the amino esters used to prepare the known polymers, they have less tendency to hydrolyze when in the monomeric form than the conventionally used amino esters, and they are therefore much more readily polymerized by emulsion polymerization. Polymers containing more than 55% by weight of residues of these esters can be prepared by emulsion polymerization, and, in fact, pure homopolymers can be prepared by this technique.

DETAILED DESCRIPTION OF THE INVENTION AND PREFERRED EMBODIMENTS

The tertiary or quaternary carbon atoms in the straight chain of at least three carbon atoms between the amino-nitrogen atom and the ester-oxygen atom are those carbon atoms which are bound to one or two additional carbon atoms, respectively. The radical $R_2$ can be a branched aliphatic or an araliphatic radical wherein the aralkyl group is a side chain on an alkylene group or is itself a part of the carbon chain between the nitrogen and oxygen atom. Preferable monomers of this structure are 3-dialkylamino-2,2-dimethylpropyl acrylate and -methacrylate and 3-dimethylaminobenzyl methacrylate. The aminoalkyl esters constitute at least 5% by weight of the polymer. At that proportion, coating materials are obtained which are in general still not soluble in gastric juice but only swellable therein, provided that no significant quantities of hydrophilic co-monomers are incorporated. The homopolymers of the amino alkyl esters are already partially soluble at a pH above the pH of gastric juice. The preferred proportions of the aminoalkyl ester in the formation of the emulsion polymer of this invention are between 10 and 90% by weight.

Suitable alkyl groups for $R_3$ and $R_4$ include lower alkyl groups such as methyl, ethyl, and butyl. $R_3$ and $R_4$ may also together form a heterocyclic aliphatic ring such as a pyrrolidine or a piperidine ring.

Monomers copolymerizable with the amino esters include water insoluble monomers, and among these, preferably esters of acrylic and methacrylic acids. The acrylic acid esters preferably contain ester alkyl groups having 1 to 8 C-atoms; the methacrylic acid esters can contain alkyl groups having 1 to 18 C-atoms. In addition to or in place of these preferred monomers other water-insoluble unsaturated copolymerizable monomers such as styrene or vinyl esters of organic carboxylic acids or maleic, fumaric or itaconic acid esters can be incorporated into the polymer. Water soluble co-monomers, such as vinylpyrrolidone, hydroxy esters of unsaturated polymerizable carboxylic acids, acrylamide or methacrylamide or their N-alkyl sustituted derivatives, insofar as they are incorporated into the polymer, are generally present in proportions less than 20% by weight. Unsaturated carboxylic acids such as acrylic, methacrylic, maleic or itaconic acids or their water soluble salts are present in general in amounts of at most 3%. The type and proportions of the monomer components are fundamentally so chosen that the polymer is soluble or at least swellable in the pH range of gastric juice, i.e., between pH 2 and 4. In order to be suitable as a pharmaceutical coating, the swellability must be sufficient to make the coating at least sufficiently permeable that active ingredients can diffuse through it.

As is known, the hardness and the elasticity of films prepared from a polymer depend upon the composition of the polymer. These properties can be adjusted according to the technical requirements of the particular application, as is known to those skilled in the art, by suitable combinations of hard monomers such as methyl methacrylate and soft monomers among which are found, for example, butyl acrylate as well as several of the amino alkyl esters used in this invention.

The molecular weight of the polymer is generally over 10,000 and, in order that the polymer can be handled in powder form or as an organic solution should not be over 1,000,000. In the latex form the polymer exists in particles of the usual size in the range of from 0.03 to 3 micrometers and can form powder aggregates of significantly larger particle diameter. However it is advantageous if such aggregates are not glazed but comprise loose aggregates of fine particles which again break up into substantially finer particles when they are agitated in water or other fluid medium. Accordingly, the powder is rapidly soluble in organic solvents.

The polymers can be prepared by the known methods of aqueous emulsion polymerization, and they contain the typical adjuvants used in these processes in the conventional amounts. They preferably contain anionic or non-ionic emulsifiers or mixtures of these types of emulsifiers; however, polymers can also be used which have been prepared by known emulsifier-free processes. The proportion of emulsifiers, calculated on the amount of aqueous phase, lies in the range from 0.1 to 10% by weight. The proportion of anionic emuosifier preferably lies between 0.01 and 2% by weight and the proportion of non-ionic emulsifiers between 0.1 and 5% by weight; the latter can also be added after the preparation of the emulsion polymer. The solids content of the dispersion is preferably in the range from 20 to 50% by weight. Especially preferred are emulsion polymers which are prepared by the monomer feed or the emulsion feed process. The pH of the aqueous polymer dispersion is in general between 7 and 12 and preferably between 8 and 10.

The aqueous dispersion of the emulsion polymer can be incorporated as such into an aqueous coating material as such as a binder. However, it is also possible to recover the emulsion polymer in powder form by known methods, for example, by precipitation, spray drying or freeze drying, and to use it as a binder for coating materials by itself or in the form of an organic solution.

Although there are cases in which the aqueous polymer dispersion is used as such for preparation of a pharmaceutical coating material, most of the coating materials used in practice for pharmaceutical dosage forms contain a rather large number of liquid or solid additives which also may be used in the compositions of this invention. Among such additives are in particular, pigments, fillers, soluble dyes, plasticizers for the binder, gloss and smoothing agents, flavorings, photostabilizers, anti-foaming agents and flow promoting materials. These additives can be incorporated into the aqueous dispersion, into the polymer in powder form, or into a solution of the polymer in an organic solvent.

The amount of the polymer of this invention contained in the coating for the drug dosage form may range from the minimum amount needed to be an effective binder for the other ingredients of the pharmaceutical coating up to 100%. The coatings for drug dosage forms typically contain from about 25% by weight up to 100%.

A number of processes can be used according to the invention to coat pharmaceutical dosage forms with the polymers of this invention or coating materials prepared from them. Thus, an aqueous dispersion of the polymer or an aqueous coating material, which has been prepared from a dispersion by incorporation of suitable additives, can be applied to the dosage forms by means of a dragee coating process or a fluidized bed coater by known procedures. Suitable procedures are described in German Pat. No. 2,135,073 or British Pat. No. 1,393,374. Small quantities of volatile organic liquids, e.g. lower aliphatic alcohols, ketones, and esters, can be combined with the above mentioned materials as plasticizers and thereby facilitate the formation of a film coating.

Other coating processes start with the polymer isolated from the aqueous phase. It can be used either by itself, in finely divided powder form, or after admixture with conventional solid additives, to coat pharmaceutical dosage forms. Among the coatable dosage forms may also be included, e.g. crystals of the active ingredient which can be compressed together with the polymer in powder form or with a powder coating composition prepared by admixture with solid additives, into shaped tablets. Granulating procedures can also be carried out with powder mixtures containing active ingredients. On the other hand, the pulverulent coating materials can be contacted with the dosage forms in a fluidized bed coater at elevated temperature, whereby the particles are sintered or melted together to form a continuous layer.

A particularly advantageous coating process is thermogelation, disclosed in U.S. patent application Ser. No. 328,486. In the thermogelation process the powder coating material is suspended in an aqueous solution of a plasticizer, wherein the plasticizer is chosen so that the emulsion polymer does not dissolve therein at room temperature, but upon heating after the evaporation of the water forms a solid gel mass. The suspension can be contacted with the dosage form in a dragee pan or in the fluidized bed coating apparatus and then it is converted to a solid gelled coating layer on its exterior surface by heating. In another embodiment of this process, the dosage forms are moistened with an aqueous solution of the plasticizer and the coating material is sprinkled on in powder form. In this case as well thermogelation occurs on the surface to form a continuous layer. Suitable plasticizers are, for example, slightly volatile polyhydroxy compounds such as polyethylene glycols, sugar alcohols, or esters of citric acid. The amounts of plasticizer are so chosen that they are sufficient for dissolving and gelling the emulsion polymer and that after cooling the coating layer is hard and not tacky.

A further preferred method for applying of the coating materials of the invention comprises preparing an organic solution from the finely divided polymer, which can be provided with additional conventional additives by known procedures. In order to obtain a good solubility of the emulsion polymer in organic solvents, it is preferable, as taught in U.S. Pat. No. 4,112,215, to use the coating material in powder form prepared by spray drying from an aqueous dispersion of the polymer such as that obtained from the emulsion polymerization. In order to prepare the solution, the conventional organic solvents used for this purpose, such as lower alcohols and ketones or their mixtures can be employed. The coating material dissolved in organic solvent can be used in all conventional processes for coating of dosage forms, as is known to those skilled in the art. The dragee pan process and the fluidized bed coating process are the most common of the processes which have been used.

Just as it is possible or feasible in known coating processes to apply the coating gradually or in several layers, this also can be done with the coating materials of this invention. In this case, the coating materials of the invention can form the entire coating or optionally a base layer, intermediate layer or outer layer, wherein additional layers having other solubility properties can be used. Individual layers of this kind in multiple-layer coatings can be formed from the pure polymer without further additives. It is not necessary to provide further discussion here regarding the very many methods of obtaining a predetermined solubility and controlled release characteristic in the gastrointestinal tract using a selected sequence of layers having different solubility properties. The diverse layers can also be applied by diverse processes. Thus, for example, a matrix tablet, whose core is composed of individual particles coated by the process of the invention can be coated with an exterior coating of another type of material, e.g. a sugar dragee material, or vice versa.

The multitude of possible application processes corresponds to the multitude of kinds of dosage forms to be coated. Crystals of active ingredient or granulates thereof, pills, dragee nuclei and tablet nuclei or filled pharmaceutical capsules can be coated by the coating material of the invention. As a single coating or as the layer soluble in gastric juice of a multiple layer coating, the layers applied according to the invention can have a thickness between 5 and 20 micrometers. The coating materials according to the invention can also be employed as binders for granulation and agglomerlation of pharmaceuticals.

Having generally described the invention, a more complete understanding can be obtained by reference to certain specific examples, which are provided herein for purposed of illustration only and are not intended to be limiting unless otherwise specified.

EXAMPLES 1-17: PREPARATION OF THE BINDERS

EXAMPLE 1

In a polymerization reactor provided with a stirrer and a heating/cooling jacket, 0.4 g of sodium lauryl sulfate was dissolved in 580 g of water and the mixture was heated to 80° C. To this was added a solution of 0.7 g of the sodium salt of 4,4-azobis(4-cyanovaleric acid) in 25 g of water.

To this solution an emulsion of the following composition was added dropwise over a period of four hours:
  180 g N,N-dimethylamino-2,2-dimethylpropyl methacrylate
  210 g methyl methacrylate
  210 g ethylacrylate
  3 g sodium lauryl sulfate
  2 g sodium salt of 4,4-azobis(4-cyanovaleric acid)
  800 g water The temperature of the reaction vessel was maintained at 80° C. After completion of the addition, the temperature was kept at 80° C. for two more hours. After cooling to room temperature a low-viscosity dispersion free of coagulation was obtained.
  solids content: 30% by weight
  pH: 9.0
  minimum film-forming temperature: 24° C.
  white point temperature: 18° C.

EXAMPLE 2

The procedure of Example 1 was followed except that after the conclusion of polymerization and cooling to 30° C. the dispersion was compounded by adding dropwise a soluton of 14 g of an addition product of isononylphenol and 100 moles of ethylene oxide in 33 g of water.

A low-viscosity dispersion was obtained: solids content: 30% by weight; pH: 8.9; minimum film-forming temperature: 24° C.; white point temperature 18° C.

EXAMPLE 3

The procedure of Example 2 was followed except that the dispersion was compounded by adding a solution of 21 g of the same additive in 50 g of water.

A low-viscosity dispersion was obtained; solids content: 30% by weight; pH: 8.8; minimum film-forming temperature: 24° C.; white point temperature 18° C.

EXAMPLE 4

In a polymerization reactor equipped with a stirrer and a heating/cooling jacket 0.4 g of sodium lauryl sulfate was dissolved in 580 g of water and heated to 80° C. Thereupon a solution of 0.7 g of the sodium salt of 4,4-azobis(4-cyanovaleric acid) in 25 g of water was added.

To this solution was added dropwise over a period of four hours an emulsion comprising:
  120 g 3-dimethylaminobenzyl methacrylate
  270 g ethylacrylate
  210 g methylmethacrylate
  3 g sodium lauryl sulfate
  2 g sodium salt of 4,4-azobis(4-cyanovaleric acid)
  800 g deionized water The temperature in the reaction vessel was maintained at 80° C. After the completion of the addition the temperature was maintained for two additional hours at 80° C. After cooling to room temperature a low-viscosity dispersion free of coagulation was obtained.
  solids content: 30% by weight
  pH: 7.5
  minimum film-forming temperature: 22° C.
  white point temperature: 17° C.

EXAMPLE 5

The procedure of Example 1 was followed using the following ingredients:

Initial solution:
4 g polyoxyethylenesorbitan monooleate
0.7 g sodium salt of 4,4-azobis(4-cyanovaleric acid)
600 g completely deionized water
Emulsion:
300 g N,N-dimethylamino-2,2-dimethylpropyl methacrylate
180 g ethyl acrylate
120 g methyl methacrylate
12 g polyoxyethylenesorbitan monooleate
2 g sodium salt of 4,4-azobis(4-cyanovaleric acid)
800 g deionized water A low-viscosity dispersion, free of coagulation was obtained; solids content: 29% by weight; minimum filmforming temperature: 15° C.; white point temperature: 5° C.

EXAMPLE 6

The procedure of Example 1 was followed using the apparatus described therein. The emulsion comprised:
180 g N,N-dimethylamino-2,2-dimethylpropyl methacrylate
6 g methacrylic acid (weight calculated as the acid, added in the form of the sodium salt)
210 g ethyl acrylate
204 g methyl methacrylate
3 g sodium lauryl sulfate
2 g sodium salt of 4,4-azobis(4-cyanovaleric acid)

A low-viscosity dispersion, free of coagulation was obtained: solids content: 30% by weight; pH: 9.1; minimum film-forming temperature: 25° C.; white point temperature: 18° C.

EXAMPLE 7

The procedure of Example 6 was followed and the dispersion was compounded after the conclusion of the polymerization by dropwise addition, at 30° C., of 30 g of an adduct of isononylphenol with 100 moles of ethylene oxide dissolved in 70 g of water.
Properties of the dispersion:
solids content: 30% by weight
pH: 8.7
viscosity: 8 mPa.sec

EXAMPLE 8

One hundred parts by weight of the dispersion of Example 3 and 100 parts by weight of a 30% aqueous dispersion of a copolymer of ethyl acrylate and methyl methacrylate were mixed to form a stable mixed dispersion: pH: 8.5; minimum film-forming temperature: 12° C.; white point temperature: 0° C.

EXAMPLE 9

A dispersion mixture was prepared from 100 parts by weight of the dispersion of Example 3 and 200 parts by weight of a 30% aqueous dispersion of a copolymer of alkyl acrylate and methyl methacrylate. A stable 30% mixed dispersion was obtained; pH: 8.3; minimum film-forming temperature: 9° C.; white point temperature: 0° C.

EXAMPLE 10

In a polymerization reactor (as in Example 1) the following initial solution was prepared:
1.8 g sodium lauryl sulfate
1.8 g sodium salt of 4,4-azobis(4-cyanovaleric acid)
1500 g water Over a period of 4 hours at 80° C. an emulsion was added comprising:
1600 g N,N-dimethylamino-2,2-dimethylpropyl methacrylate
720 g methyl methacrylate
24 g 2-ethylhexyl thioglycolate
16 g sodium lauryl sulfate
5 g sodium salt of 4,4-azobis(4-cyanovaleric acid)
2350 g of water After subsequent heating for two hours at 80° C. the reaction mixture was cooled to room temperature. An easily filterable dispersion of about 40% solids content with low viscosity was obtained. After removal of small amounts of a coagulum (about 10 g) by filtration, the dispersion was spray-dried. A powder comprised of white, unglazed granules having a diameter of about 30 micrometers was obtained. Apparent density: 410 g/l; residual mositure: 0.1%.

EXAMPLES 11–17

Additional dispersions were prepared by the procedures of Examples 1 and 5 having varied compositions of the monomer mixtures. The proportions of monomers and the properties of the dispersions are given in Table 1. The dispersions of Examples 1 and 5 are included in the table for comparison.

TABLE 1

| Example No. | Preparation Procedure | Monomer composition (wt. %) | | | MFT (°C.) | CP (°C.) |
|---|---|---|---|---|---|---|
| | | M | EA | MMA | | |
| 11 | Example 1 | 30 | 45 | 25 | 9 | 2 |
| 1 | — | 30 | 35 | 35 | 24 | 18 |
| 12 | Example 1 | 30 | 25 | 45 | 43 | 35 |
| 13 | Example 5 | 50 | 40 | 10 | 0 | 0 |
| 5 | — | 50 | 30 | 20 | 15 | 5 |
| 14 | Example 5 | 50 | 25 | 25 | 26 | 19 |
| 15 | Example 5 | 50 | 20 | 30 | 35 | 25 |
| 16 | Example 1 | 90 | 10 | — | 25 | 16 |
| 17 | Example 1 | 100 | — | — | 49 | 37 |

M = N,N—Dimethylamino-2,2-dimethylpropyl methacrylate
EA = Ethyl acrylate
MMA = Methyl methacrylate
MFT = Minimum film-forming temperature
CP = White point temperature Examples 18–20: Preparation of Pharmaceutical Coatings

EXAMPLE 18

75 grams of the aqueous dispersion of Example 4, containing 22.5 grams of dry resinous material, were mixed with a colored pigment, talc, a white pigment and PEG 6000 to form a 20.6% suspension and sprayed onto 3 kg of tablets in a dragee pan having a diameter of 35 centimeters. An air pressure spray gun having a nozzle diameter of 1.0 mm was used as a spray apparatus. The spray suspension was supplied to the spray gun by a tube pump (tube diameter: 3 mm) and sprayed with a spray pressure of 0.5 bar. The spray rate during the continuous spraying process was 2.1 grams of sprayed suspension per minute per kg of tablets. During the spray coating, warm air at 70° C. (about 2 m³/min) was blown onto the rotating tablets, whereby the tablet temperature was about 35° C.

Film coated tablets were obtained having a uniform smooth and glossy overcoating, which disintegrated and dissolved in water and artificial gastric juice BP in at most 5 minutes. The breaking strength was increased from 8 kp to 10 kp. The amount of dry resinous material sprayed onto the tablets amounted to 0.7 mg per cm$^2$ of tablet surface, or 0.75%, calculated on the amount of tablets. The total dry material amounted to 2.75% of the tablet amount. This corresponded to a total film thickness of about 20 micrometers.

The dispersions of Examples 1 to 3 were used in the same way and gave equivalent coatings.

EXAMPLE 19

75 grams of the dispersion of Example 6, containing 22.5 grams of dry resinous material, where compounded with colored pigments, talc, white pigment and PEG 6000 to form a dragee suspension and sprayed onto 3 kg of tablets under the same conditions as in Example 18. The spray rate was 2.3 grams of sprayed suspension per minute per kg of tablets.

A smooth, uniform and glossy film coating was obtained which disintegrated and dissolved in water and artifical gastric juice within 3 minutes. The breaking strength of the tablets increased from 8 kp to 9 kp.

The dry resinous material and the total dry material were used in the same quantities as in Example 18.

The dispersions of Example 7-9 were used in the same manner and yielded equivalent coatings.

EXAMPLE 20

In a solvent mixture of 522 g of isopropenol and 348 g of acetone, 130 g of the spray dried emulsion polymer of Example 10 were dissolved at room temperature in 25 minutes to form a clear, colorless solution. 265 g of this solution containing 33 g of dry resinous material were continuously sprayed, together with talc, magnesium stearate, white pigment, colored pigment and PEG 6000, onto 3 kg of tablets in a dragee pan having a diameter of 35 centimeters. The sprayed suspension contained 9.85% solids. An air pressure spray gun having a nozzle diameter of 1.0 mm was used as the spraying apparatus. The sprayed suspension was supplied to the spray gun by means of a tube pump (tube inner diameter: 3 mm) and subsequently sprayed onto the tablets in the rotating dragee pan using an air pressure of 0.5 bar. During the spraying process warm air at about 45° C. (2 m$^3$/min) was blown onto the tablet bed, so that the temperature of the tablets was about 33° C. The spray rate was 7 g of suspension per minute per kg of tablets.

Smooth, uniform and glossy film coatings were obtained which disintegrated in water in at most 5 minutes and dissolved in artifical gastric juice BP within 3 minutes. The breaking strength of the tablets remained the same.

An amount of 1 mg of dry resinous material per cm$^2$ of tablet surface, or 1.1% calculated on the amount of tablets, was sprayed on. The total dry material amounted to 4.4% calculated on the amount of tablets. This corresponds to an overall coating thickness of about 30 micrometers.

Having now fully described the invention, it will be apparent to one of ordinary skill in the art that many changes and modifications can be made thereto without departing from the spirit or scope of the invention as set forth herein.

What is claimed as new and sought to be protected by Letters Patent of the United States is:

1. A pharmaceutical dosage form coated with a synthetic polymer, soluble or swellable in gastric juice, prepared by emulsion polymerization comprising
   (1) 5–100% by weight of units derived from an aminoalkyl ester monomer of the formula

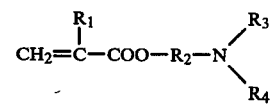

wherein:
   $R_1$=hydrogen or a lower alkyl group,
   $R_2$=2,2-dimethyl propyl or benzyl,
   $R_3$ and $R_4$=lower alkyl groups or together with the N atom form a penta or hexa atomic heterocyclic ring; and
   (2) 0–80% by weight of a copolymerizable monomer selected from the group consisting of esters of acrylic acid and methacrylic acid.

2. The dosage form of claim 1 wherein $R_1$ is a lower alkyl group.

3. The dosage form of claim 1 wherein said aminoalkyl ester is N,N-dimethylamino-2,2-dimethylpropyl methacrylate.

4. The dosage form of claim 1 wherein residues of said aminoalkyl ester constitute 10–90% by weight of said polymer.

5. A synthetic dosage form with a coating comprising
   (a) 25–100% by weight of the polymer of any one of claims 1, 2 or 3 and
   (b) 0–25% by weight of a pharmaceutically acceptable non-toxic coating additive selected from the group consisting of pigments, fillers, dyes, plasticizers, gloss improvers, smoothing agents, flavors, photostabilizers, anti-foaming agents, and flow improving materials.

6. The dosage form of claim 1 wherein said dosage form is a dosage form suitable for oral administration.

7. The dosage form of claim 1 wherein said dosage form is selected from the group consisting of crystals, granules, pills dragees, tablets, and capsules.

* * * * *